(12) United States Patent
Lawson et al.

(10) Patent No.: US 6,477,895 B2
(45) Date of Patent: Nov. 12, 2002

(54) RUB-OFF TEST METHOD AND APPARATUS

(75) Inventors: John R. Lawson, Pittsford, NY (US);
Gerald Darby, II, Brockport, NY (US);
Joseph A. Basile, Hilton, NY (US)

(73) Assignee: Heidelberger Druckmaschinen AG, Heidelberg (DE)

( * ) Notice: Subject to any disclaimer, the term of this patent is extended or adjusted under 35 U.S.C. 154(b) by 0 days.

(21) Appl. No.: 09/804,863

(22) Filed: Mar. 13, 2001

(65) Prior Publication Data

US 2002/0129637 A1 Sep. 19, 2002

(51) Int. Cl.$^7$ .............................................. G01N 21/25
(52) U.S. Cl. ........................................................ 73/150 R
(58) Field of Search ...................... 73/7, 150 A, 150 R; 356/402, 408, 425

(56) References Cited

U.S. PATENT DOCUMENTS

| | | | | | |
|---|---|---|---|---|---|
| 3,063,285 A | * | 11/1962 | Jensen et al. | ..................... | 73/7 |
| 3,412,605 A | * | 11/1968 | Oehme et al. | ................. | 73/150 |
| 5,073,028 A | * | 12/1991 | Bowden et al. | | |
| 5,140,902 A | * | 8/1992 | Schneider | ................. | 73/150 R |
| 5,854,680 A | * | 12/1998 | Rakitsch | | |
| 6,018,385 A | * | 1/2000 | Lampersberger et al. | | |

OTHER PUBLICATIONS

Sutherland Ink Rub Tester, Description and Procedures, Danilee Co., No Date.
GAT V Abrasion Tester, Gavarti Associates, undated.
ASTM Designations D–5264–92 & D–5181–91, American Society for Testing and Materials, undated.

* cited by examiner

Primary Examiner—Robert Raevis

(57) ABSTRACT

A method and apparatus for measuring rub-off from an image-bearing substrate.

17 Claims, 3 Drawing Sheets

FIG. 1

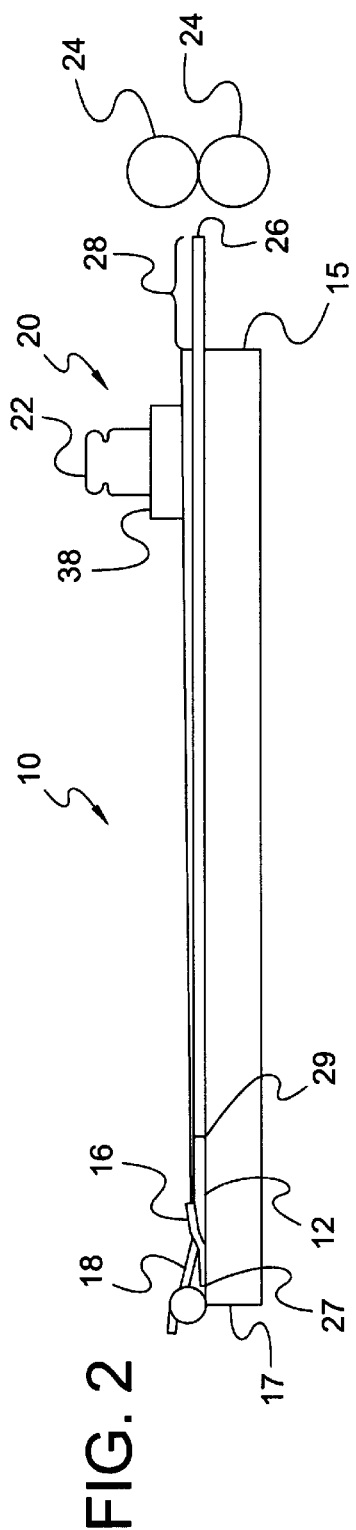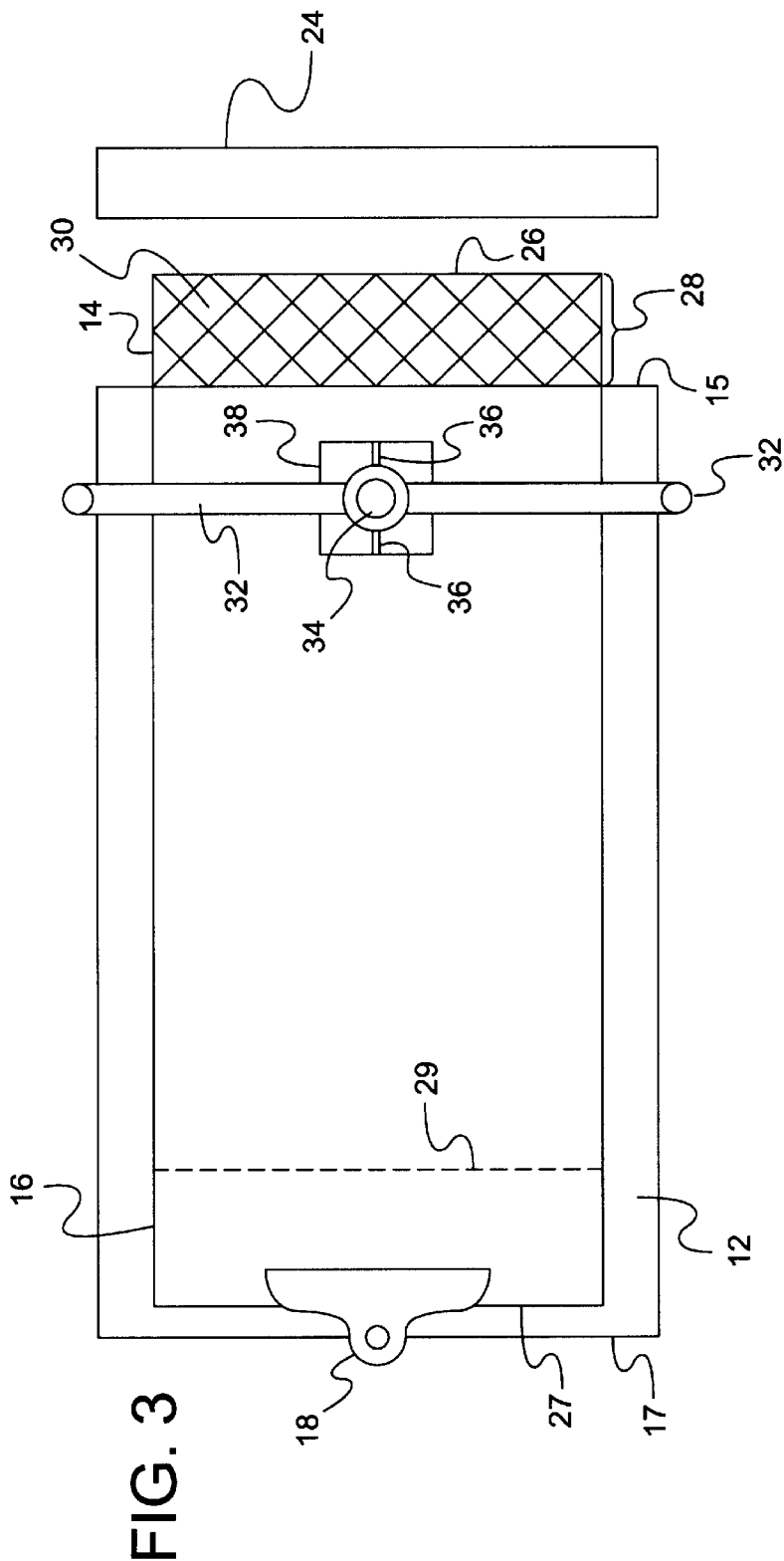

RUB-OFF TEST METHOD AND APPARATUS

FIELD OF THE INVENTION

This invention relates to the field of image quality and specifically image permanence of a toner image produced by electrophotographic methods. The apparatus and method of the present invention are directed to an analysis of the permanence of the image and comprise an apparatus and method designed to effectively and reproducibly test the effect of controlled abrasion on a test image.

BACKGROUND OF THE INVENTION

The production of images using a toner on plain paper by electrophotographic means is common and well known. As printers employing electrophotography increase in speed and image quality, they are found in environments outside the realm of office copiers. These other environments often employ finishing equipment, such as folders, to make a finished product including the images on paper produced by the printer. These devices require means to move and control the position of the printed sheets relative to each other.

To achieve this control, the finishing equipment must come in contact with the image-bearing sheets. In some equipment this contact for handling of the image can abrade the image. This abrasion can manifest itself in several ways, but in general it is a smudge on another page (rub-off) and detracts from the overall quality of the image of a second sheet.

Attempts to quantify the amount of abrasion or rub-off of the image have resulted in various testing methods and apparatus. The apparatus has consisted of a moveable platen, a friction motor drive and weights used together to provide a controllable means to generate rub-off.

The prior art apparatus basically supported a test sheet of a material to be evaluated on a platen, face up, with the leading edge of the test sheet extending beyond the front end of the platen. A standard material receiver sheet was then placed over the test sheet with its leading edge aligned with the front edge of the platen. A known weight providing pressure similar to the pressures used in finishing equipment was then placed on top of the papers completing the stack. The location of the weight was just behind the front edge of the platen. The test sheet was then pulled out from under the receiving sheet. The area where the weight rests on both sheets (test area) was then analyzed for toner residue from the test sheet. The amount of toner in the test area on the receiver sheet has been shown to correlate with the subjective impressions of the amount of rub-off from copies produced by a given system.

Other abrasion testers are known to the art. The Sutherland Rub Tester and the GAT V Abrasion Tester are devices that follow ASTM standards for abrasion of printing inks.

These tests are identified by ASTM Designations D-5264-92 and D-5181-91. These procedures, however, are considered to be much more aggressive procedures and are not considered suitable for the rub-off levels encountered in current toner-based systems. Previously used tests have been very susceptible to the subjective interpretation of the test operator.

Accordingly, since the reduction and control of rub-off from copies produced from modern copy machines is of increasing interest, a continuing effort has been directed to developing a more reproducible test method which is not susceptible to subjective interpretation by the test operator.

SUMMARY OF THE INVENTION

According to the present invention, rub-off from an image-bearing substrate is tested by positioning a test substrate having an image-bearing side bearing a plurality of images and a receiver substrate in contact at a test area at a selected pressure; moving the test substrate relative to the receiver substrate a selected distance through the test area; and, determining the relative amount of rub-off in the test area on the receiver by use of a calibrated scanner.

The present invention further comprises a method for measuring rub-off from an image-bearing substrate, the method comprising: positioning a test substrate having a first and a second side with its first side bearing a plurality of images on a flat surface with its second side supported by the flat surface; positioning a receiver substrate over the test substrate and restricting movement of the receiver substrate relative to the flat surface; positioning a selected weight above the receiver substrate at a selected location so that the weight urges the receiver substrate into engagement with the test substrate in a test area; moving the test substrate a selected distance relative to the receiver substrate through the test area; and, determining the relative amount of rub-off in the test area on the receiver substrate by use of a calibrated scanner.

The present invention further comprises a method of measuring rub-off from an image-bearing substrate, the method comprising: positioning a receiver substrate having a first and a second side on a flat surface with one of its sides supported by the flat surface; positioning a test substrate having a first and a second side with its first side bearing a plurality of images over the receiver substrate with its first side supported on the receiver substrate; restricting movement of the receiver substrate relative to the flat surface; positioning a selected weight above the test substrate at a selected location so that the weight urges the test substrate into engagement with the receiver substrate in a test area; moving the test substrate a selected distance relative to the receiver substrate through the test area; and, determining the relative amount of rub-off in the test area on the receiver substrate by use of a calibrated scanner.

The present invention also comprises an apparatus for measuring rub-off from an image-bearing substrate, the apparatus comprising: a flat surface having a first and a second end, a length and adapted to support a first substrate with one of its ends extending beyond the first end of the flat surface; a restrainer for preventing movement of a second substrate along the length of the flat surface; a pressure pad adapted to impose a selected pressure on the first substrate and the second substrate in a test area; a puller adapted to pull the first substrate a selected distance through the test area relative to the second substrate; a calibrated scanner; and, a computer program for converting the scanner results into a numerical test result.

BRIEF DESCRIPTION OF THE DRAWINGS

FIG. 1 is a test pattern used for rub-off tests according to the present invention;

FIG. 2 is a side view of an apparatus useful in the practice of the present invention;

FIG. 3 is a top view of the apparatus shown in FIG. 2; and,

DESCRIPTION OF THE PREFERRED EMBODIMENTS

Figure 4:
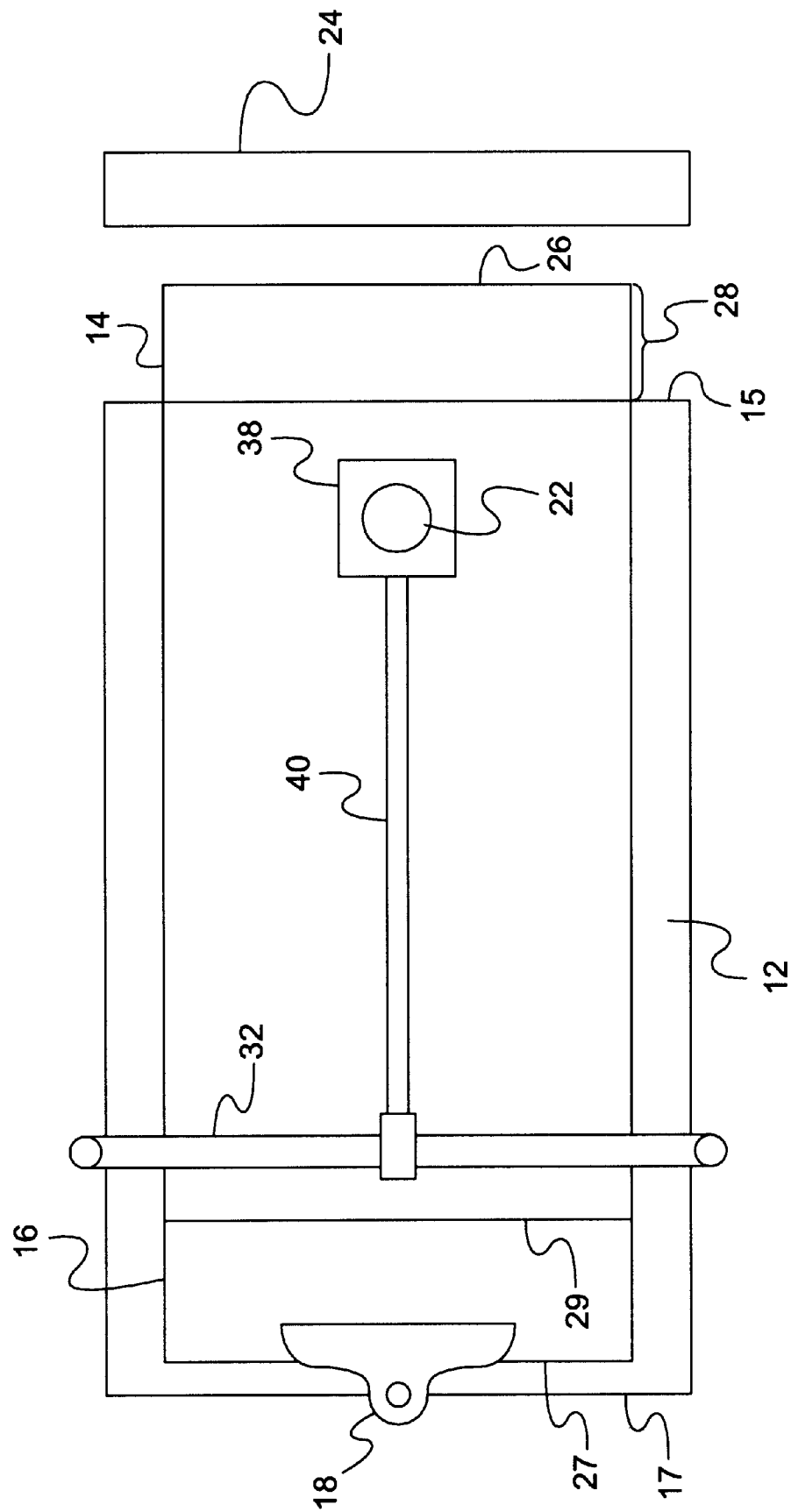
FIG. 4 is a top view of an alternate embodiment of the apparatus shown in FIG. 2.

In the description of the Figures, the same numbers will be used throughout to refer to the same or similar components.

The present invention comprises a repeatable and accurate method for quantifying the test results produced by the test apparatus. The test is applicable both to toner images and printer images and other images on a variety of substrates, although typically the images analyzed are toner images on paper. Both the first and second substrate used in the test are paper of various grades and weights, but are typically the same paper for each test.

Figure 1:
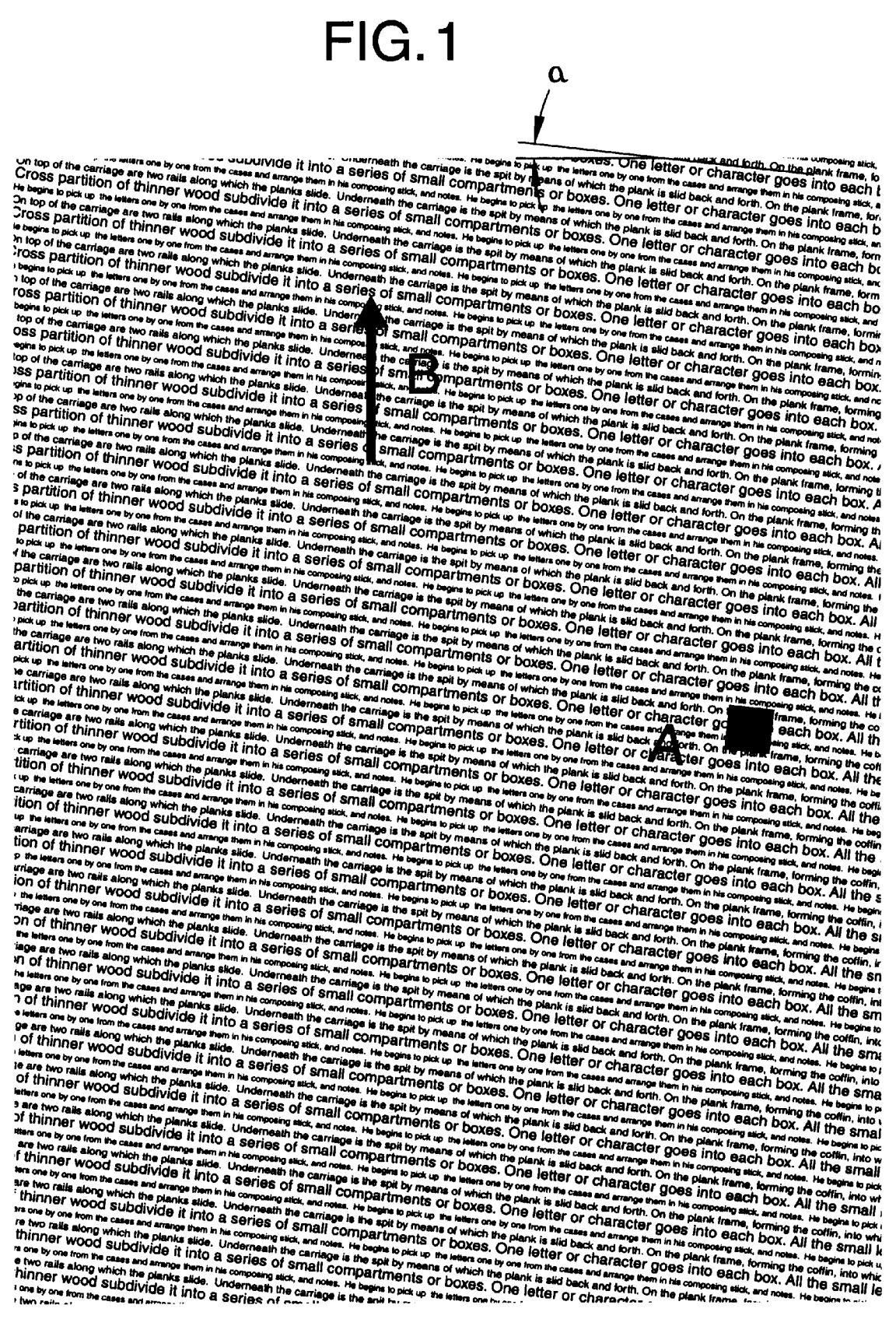

In FIG. 1, a sheet bearing a test pattern ready for testing is shown. This sheet is a very closely spaced printed sheet, which is copied for purposes of testing the product from a particular copying or printing system for rub-off. The image contains a very dense black square indicated at "A" this image is used for quality control purposes to allow measurement of density. The test area defined by 36 in FIG. 3 can be of any suitable size, although an area of approximately 0.7 inches by 0.7 inches is preferred. This test area represents an area of approximately one-half inch and allows for easy calculation of the required weight. The test sheet is generally moved relative to a receiver sheet in the direction shown by arrow "B", although the movement could be in any other direction if desired.

Typically, the text is written at an angle or the test pattern sheet is trimmed so that it is oriented at an angle "a" as shown in the upper left of FIG. 1 of about 7 degrees. Any suitable angle could be used and the angle of the text or the sheet is trimmed in this fashion to result in moving the image on the test sheet relative to the receiver sheet at an angle to the test pattern. It is considered that this provides an improved result.

In FIG. 2, a test apparatus for the conduct of the present method is shown. A flat surface 12 is shown with a first sheet 14 positioned on the flat surface. A first end 26 of the first sheet 14 extends a distance 28 beyond a front end 15 of the flat surface as shown.

In the embodiments shown in FIGS. 2 and 3, a test pattern 30 is placed on the upper surface of the first sheet. A second sheet 16 is positioned over the first sheet with its first end 27 extending to near a back end 17 of the flat surface. A pressure pad 38 bearing a weight 22 is positioned near the front end of flat surface 12. The pressure pad could be positioned at any desired location but it is conveniently positioned near the front end of flat surface 12. The second sheet is retained in position by a clip 18 or any other effective restraining device so that it cannot move relative to flat surface 12. As shown, a pair of rollers 24 are used to pull first sheet 14 from its position on flat surface 12 and beneath second sheet 16 beneath pressure pad 38. This results in controlled abrasion in a test area "A" as shown in FIG. 1 beneath pressure pad 38. The rollers provide a controlled pulling rate. Either roller 24 may be movable into engagement with first end 26 of first sheet 14 or flat surface 12 may be moveable to move first end 26 of first sheet 14 into engagement with rollers 24. Second sheet 16 is retained in position relative to flat surface 12 and a square area of discoloration (test area) representative of the rub-off produced by the removal of first sheet 14 will be produced in the test area beneath pressure pad 38 on the second sheet (receiver sheet). The second sheet is then tested to quantify the amount of rub-off resulting from the movement of first sheet 14 relative to second sheet 16.

In FIG. 3, a top view of the apparatus shown in FIG. 2 is shown. It will be noted that in this view, pattern 30 is visible on the top of the extended portion of first sheet 14. Pressure pad 38 is shown supported from a support 32 and is shown schematically as mounted on a rod 34 slideably positioned through support member 32 with extensions 36 to provide an open surface on the top of pressure pad 38 for the positioning of weights and the like.

Any suitable method or apparatus may be used to restrain the pressure pad and impose the desired pressure on the test area. Desirably, in each test, a second end 29 of the first sheet is positioned at the same point relative to the front of flat surface 12. This permits a pull of the same length for each test. To achieve the optimum results, desirably the same type of paper is used for the second sheet 16 and the same length of pull is used in all tests. The amount of weight on pressure pad 38 can be varied or can remain the same through all the tests. In some instances, it is desirable to vary the weight and in other instances it may be more desirable to run all the tests at the same weight. Substantially any grade of paper can be used, both for the first sheet and for the second sheet. The grade of paper used for the sheets may be the same or it may be different.

In FIG. 4, an alternate embodiment of the apparatus shown in FIG. 2 is shown. In this embodiment a pivot arm 40 is used to restrain pressure pad 38 in position on flat surface 12. Further in this embodiment, the printed test sheet is the (upper) sheet 16 with the clean receiver sheet being lower sheet 14. The test sheet is positioned with its image-bearing side supported on the receiver sheet with the test sheet being withdrawn by rollers 24 as described above with movement of the receiver sheet relative to the flat surface being restricted. The same criteria apply since the important criteria are those that relate to the movement of the test sheet relative to the receiver sheet with the desired weight (pressure) applied to pressure pad 38.

The test apparatus comprises: a flat surface having a first and a second end and a length and adapted to support a first substrate with one of its ends extending beyond the first end of the flat surface; a restrainer for preventing movement of a second substrate along the length of the flat surface; a test area adapted to impose a selected pressure on the first substrate and the second substrate in the test area; a puller adapted to pull the first substrate a selected distance through the test area relative to the second substrate; a calibrated scanner; and, a computer program for converting the scanner results into a numerical test result.

The method disclosed herein requires positioning the test and receiver substrates so that the test substrate is moved relative to the receiver substrate at a controlled rate for a controlled distance at a selected pressure. The amount of pressure used can vary from about 0.5 to about 5 pounds per square inch (psi) or more if desired. Preferably, the pressure is from about 1 to about 4 psi.

The selected distance is typically greater than about 6 inches. Desirably, a relatively dense pattern of images comprises the test pattern. When more printing is available on the test sheet, better results are obtained. The test pattern is desirably copied or printed by the system to be tested and the same pattern is desirably used for all comparable tests.

In the present method, the receiver sheets may be analyzed by scanning the images (rub-off smudges) on a calibrated desktop scanner. The scanned digital images are then stored for later analysis. The images are read into an analysis program and the standard deviation of the density values of the image is calculated. The standard deviation is chosen because it provides a larger signal-to-noise value at low rub-off values than other measures (i.e., the total toner area or total density of a test patch). Desirably six test repetitions are used. The six test area standard deviations are then averaged and the confidence limits calculated if a single weight was used. This provides the test results as a numerical result, which is determined without the necessity for a subjective interpretation of the discoloration on the second sheet in the test area. It has been found by the use of the calibration used for the interpretation of references that on a scale from 1 to 25, the discoloration of the receiver sheet in the test area using a clean piece of paper as the test sheet is about 3. Readings up to the low twenties have been observed for test sheets bearing toner images by the method of the present invention. The method of the present invention provides accurate repeatable test results.

The apparatus may be of a variety of configurations, provided that it provides a flat surface and a means for positioning the first sheet with the test pattern for movement relative to the second sheet beneath a test area, having a pressure pad, a comparable distance for each test under comparable conditions.

It should be understood that the first sheet may bear the test pattern image or the test pattern image may be on the second sheet. In either event, accurate and predictable results are achieved. It is preferred that the movement of the test sheet relative to the receiver sheet be at least 6 inches. As indicated previously, the pressure on the pressure pad is desirably from about 1 to about 4 pounds per square inch.

A representative rub-off procedure is as follows. The measurement of rub-off is accomplished in two steps. The first step is to abrade the material under test on the apparatus described above. The second is to take the results of the test abrasion and analyze them to obtain a quantitative measure of the rub-off characteristics of the material under investigation.

The first step of generating the test samples is accomplished by making prints on the system to be evaluated. The test prints for rub-off are made up with text printed over the entire imaging area of an 8.5×11 inches sheet. A representative test sheet is shown in FIG. 1. In FIG. 1, the text is written at seven degrees relative to the horizontal. This is to eliminate streaks in the final image where breaks between words exist. In typical use, this target is rendered as a postscript file and sent to the printer. The printer then uses this input file to generate prints for evaluation under specific test conditions. Typically a standard paper, such as Hammermill Bond, is used for test-to-test consistency.

Once the test prints have been made on the printer under study, the evaluation samples are made. These are generated by rubbing the test prints against the receiver sheet in a controlled manner. This control is obtained through the use of the test apparatus. The apparatus is shown schematically in FIGS. 2 and FIG. 3.

To use the apparatus, the following steps are followed:
1. The test sheet (first sheet) is placed on the first surface, face up. The sheet is aligned to a registration mark so that the leading edge of the test sheet protrudes beyond the front edge of the first surface.
2. The receiver sheet (second sheet) is placed on the test sheet. The receiver sheet is aligned with the leading edge of the platen. The other end is clamped in place.
3. A known weight is then placed in a holder and rests on the paper stack. The weight therefore provides a known pressure on the stack in a test area.
4. The platen is then moved laterally until the leading edge of the test sheet engages a roller nip. The rollers turn and "grab" the test sheet and pull it out from under the receiver sheet. The relative motion between the test sheet and the receiver sheet causes the toner from the test sheet to be abraded by the receiver sheet in the test area. This results in a "toner smear" image on the receiver sheet. The level of "smearing" in the test area has been shown to correlate with the subjective measure of rub-off.
5. Steps 1 to 4 are repeated six times. The replicates may be handled in one of two ways. In the first method all six replicates are done with a pressure of 3 pounds per square inch (psi). In the second method, two samples are made at each of three pressures, 1, 2, and 3 psi. The differences in the analysis of the two methods are given in the next section.

To analyze the test sheets, the following procedure is followed:
1. The toner smear in each test area is scanned on a calibrated scanner. The scanner is calibrated as follows:
   a) a step tablet of known density is scanned using the same scan conditions as used when the print is scanned;
   b) the contrast and zero point of the scanner are adjusted so that the digital values for the step tablets are at a predetermined value, within limits; and,
   c) the values of the step tablet are periodically checked when doing many scans (e.g., once an hour).
2. With the calibrated scanner, the six toner smears from each test are scanned. The scan options are selected to give the six scanned test areas sequential names. The scans are 230×230 pixels at 600 dots per inch in grayscale mode. The results are stored on the file server.
3. The data in the scanned files represent the luminance of the pixels in the scanned area. 0=black and 255=white. For each patch, the standard deviation of the luminance values is calculated. Standard deviation has been shown to provide a measure with a good signal-to-noise ratio that correlates with subjective evaluations of rub-off.
4. If all six tests were made using the same weight, the standard deviation values for luminance are averaged and the average value is reported as the rub-off for the sample under test.
5. If the six tests are made using three weights, the six standard deviation values are regressed against the pressures at which they were tested. A least squares regression curve preferably a second order linear regression, is fit through this data and the estimated values for rub-off at predetermined pressures are calculated. These rub-off values as a function of pressure are the results reported for the test.
6. Confidence limits on the reported values are calculated for both data analysis methods.

In the description of the apparatus, it is noted that two different methods for supporting the pressure pad were disclosed. A wide variety of apparatus can be used to maintain the pressure pad in position. Basically, the pressure pad must be maintained in position so that it can exert the desired pressure on the top of the second sheet while being retained in position relative to the flat surface when either of the sheets is moved. This is accomplished by either of the systems shown, but could also be accomplished by a variety of other mechanical configurations. Such configurations are obvious to those skilled in the art.

While any type of substrates bearing images may be tested, the substrates most commonly tested will be paper.

While the present invention has been described by reference to certain of its preferred embodiments, it is pointed out that the embodiments described are illustrative rather than limiting in nature and that many variations and modifications are possible within the scope of the present invention. Many such variations and modifications may be considered obvious and desirable by those skilled in the art based upon a review of the foregoing description of preferred embodiments.

Having thus described the invention, we claim:

1. An accurate and repeatable method for measuring rub-off from a toner image-bearing substrate, the method comprising:
   a) positioning a test substrate having a toner image-bearing side bearing a plurality of toner images and a receiver substrate in contact at a test area at a selected pressure;
   b) moving the test substrate relative to the receiver substrate a selected linear distance through the test area;
   c) determining the relative amount of rub-off in the test area on the receiver substrate by scanning the test area on the receiver substrate with a calibrated scanner the scanner being calibrated on step tablets of known density at the same conditions used to scan the test area; and,
   d) determining a standard deviation value for each test area, the standard deviation values providing an indication of rub-off from the test substrate.

2. The method of claim 1 wherein the substrates are paper.

3. The method of claim 1 wherein the plurality of images comprise a test pattern.

4. The method of claim 1 wherein the selected pressure is from about 0.5 to about 5 pounds per square inch.

5. The method of claim 1 wherein the selected distance is greater than about 6 inches.

6. The method of claim 1 wherein the amount of rub-off is reported as a number value representative of the standard deviation value for the test area.

7. An accurate and repeatable method for measuring rub-off from a toner image-bearing substrate, the method comprising:
   a) positioning a test substrate having a first and a second side with its first side bearing a plurality of toner images on a flat surface with its second side supported by the flat surface;
   b) positioning a receiver substrate over the test substrate and restricting movement of the receiver substrate relative to the flat surface;
   c) positioning a selected weight above the receiver substrate at a selected location so that the weight urges the receiver substrate into engagement with the test substrate in a test area;
   d) moving the test substrate a selected linear distance relative to the receiver substrate through the test area;
   e) determining the relative amount of rub-off in the test area on the receiver substrate by scanning the test area on the receiver substrate on a calibrated scanner the scanner being calibrated on step tablets of known density at the same conditions used to scan the test area; and,
   f) determining a standard deviation value for each test area, the standard deviation values providing an indication of rub-off from the test substrate.

8. The method of claim 1 wherein the test substrate and the receiver substrate are paper.

9. The method of claim 7 wherein the test substrate receiver substrate is paper.

10. The method of claim 7 wherein the test area is subjected to a pressure equal to from about 0.5 to about 5 pounds per square inch.

11. The method of claim 7 wherein the selected distance is greater than about 6 inches.

12. An accurate and repeatable method of measuring rub-off from a toner image-bearing substrate, the method comprising:
   a) positioning a receiver substrate having a first and a second side on a flat surface with one of its sides supported by the flat surface;
   b) positioning a test substrate having a first and a second side with its first side bearing a plurality of toner images over the receiver substrate with its first side supported on the receiver substrate and restricting movement of the receiver substrate relative to the flat surface;
   c) positioning a selected weight above the test substrate at a selected location so that the weight urges the test substrate into engagement with the receiver substrate in a test area;
   d) moving the test substrate a selected linear distance relative to the receiver substrate through the test area;
   e) determining the relative amount of rub-off in the test area on the receiver substrate by scanning the test area on the receiver substrate on a calibrated scanner the scanner being calibrated on a step tablets of known density at the same conditions used to scan the test area; and,
   f) determining a standard deviation value for each test area, the standard deviation values providing an indication of rub-off from the test substrate.

13. The method of claim 12 wherein the test substrate and the receiver substrate are paper.

14. The method of claim 12 wherein the selected distance is greater than about 6 inches.

15. The method of claim 12 herein the test area is subjected to a weight equal to from about 0.05 to about 5 pounds per square inch.

16. The method of claim 1 wherein a plurality of tests are performed by repeating steps a) through d) at different pressures to produce a plurality of standard deviation values at a plurality of pressures and regressing the standard deviation values against the plurality of pressures at which the tests were performed and rub-off values at the pressures at which the tests were performed are reported.

17. The method of claim 1 wherein a plurality of tests are performed by repeating steps a) through d) the same pressure and averaging the resulting standard deviation values.

* * * * *